(12) United States Patent
Balkwill et al.

(10) Patent No.: US 10,241,118 B2
(45) Date of Patent: Mar. 26, 2019

(54) CCL22 AND CCL17 CANCER BIOMARKERS

(71) Applicant: CANCER RESEARCH TECHNOLOGY LTD, London (GB)

(72) Inventors: Frances Balkwill, London (GB); Chiara Berlato, London (GB); Laura Fletcher, London (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 0 days.

(21) Appl. No.: 14/782,929

(22) PCT Filed: Apr. 9, 2014

(86) PCT No.: PCT/GB2014/051096
§ 371 (c)(1),
(2) Date: Oct. 7, 2015

(87) PCT Pub. No.: WO2014/167316
PCT Pub. Date: Oct. 16, 2014

(65) Prior Publication Data
US 2016/0041187 A1 Feb. 11, 2016

(30) Foreign Application Priority Data
Apr. 9, 2013 (GB) .................................. 1306394.6

(51) Int. Cl.
| | | |
|---|---|---|
| A61K 39/00 | (2006.01) | |
| C07K 16/40 | (2006.01) | |
| G01N 33/68 | (2006.01) | |
| G01N 33/574 | (2006.01) | |

(52) U.S. Cl.
CPC ......... *G01N 33/6863* (2013.01); *C07K 16/40* (2013.01); *G01N 33/57484* (2013.01); *A61K 2039/505* (2013.01); *G01N 2333/521* (2013.01); *G01N 2333/523* (2013.01); *G01N 2800/52* (2013.01); *G01N 2800/56* (2013.01); *G01N 2800/7028* (2013.01)

(58) Field of Classification Search
None
See application file for complete search history.

(56) References Cited

U.S. PATENT DOCUMENTS

| | | | | |
|---|---|---|---|---|
| 2005/0220787 A1* | 10/2005 | Lobo | .................. | C07K 16/2866 424/143.1 |
| 2009/0182140 A1* | 7/2009 | Furukubo | ............ | C07D 237/24 540/552 |
| 2010/0144646 A1* | 6/2010 | Paterson | ............ | G01N 33/6893 514/1.1 |
| 2010/0310464 A1 | 12/2010 | Cicortas Gunnarsson et al. | | |
| 2011/0059103 A1* | 3/2011 | Biessen | .............. | G01N 33/6863 424/158.1 |
| 2011/0306622 A1 | 12/2011 | Lannutti et al. | | |

FOREIGN PATENT DOCUMENTS

| | | | |
|---|---|---|---|
| WO | 00/42074 | | 7/2000 |
| WO | 2009/037454 | | 3/2009 |
| WO | WO2009/034470 | * | 3/2009 |
| WO | WO2009/037454 | * | 3/2009 |

OTHER PUBLICATIONS

Nakagami et al, European Journal of Pharmacology, 2009, vol. 624, pp. 38-44 (Year: 2009).*
International Search Report dated Jul. 29, 2014 in corresponding International Application No. PCT/GB2014/051096.
Shimauchi et al., "Production of Thymus and Activation-Regulated Chemokine and Macrophage-Derived Chemokine by CCR4 + Adult T-Cell Leukemia Cells", *Clinical Cancer Research*, 2005, No. 11: pp. 2427-2435.
Olsnes et al., "*In Vitro* induction of a Dendritic Cell Phenotype in Primary Human Actute Myelogenous Leukemia (AML) Blasts Alters the Chemokine Release Profile and Increases the Levels of T Cell Chemotactic CCL17 and CCL22", *Journal of Interferon & Cytokine Research*, 2008, vol. 28, No. 5, pp. 297-310.
Mizukami et al., "CCL17 and CCL22 chemokines within tumor microenvironment are related to accumulation of Foxp3+ regulatory T cells in gastric cancer", *International Journal of Cancer*, 2008, vol. 122, No. 10, pp. 2286-2293.
Ishida et al., "CCR4 as a novel molecular target for immunotherapy of cancer", *Cancer Science*, 2006, vol. 97, No. 11, pp. 1139-1146.
Nakanishi et al., "Expression of macrophage-derived chemokine (MDC)/CCL22 in human lung cancer", *Cancer Immunology, Immunotherapy*, 2006, vol. 55, No. 11, pp. 1320-1329.
Wagsater et al., "Quantification of the chemokines CCL17 and CCL22 in human colorectal adenocarcinomas", *Molecular Medicines Reports*, 2008, vol. 1, No. 2, pp. 211-217.

* cited by examiner

*Primary Examiner* — Karen A. Canella
(74) *Attorney, Agent, or Firm* — Wenderoth, Lind & Ponack, L.L.P.

(57) ABSTRACT

The present invention provides methods of obtaining information relevant to monitoring and diagnosing cancer, particularly monitoring the progression or development of cancer, monitoring the response of cancer to treatment, diagnosing cancer, making a cancer prognosis, predicting the likelihood of a cancer responding to treatment and stratifying subjects having cancer. The methods involve determining the ratio of circulating CCL17 to circulating CCL22 in a sample from a subject.

23 Claims, 11 Drawing Sheets

A

B

A

B

A

B

CCL17:CCL22

CCL22 AND CCL17 CANCER BIOMARKERS

FIELD OF THE INVENTION

Figure 1:
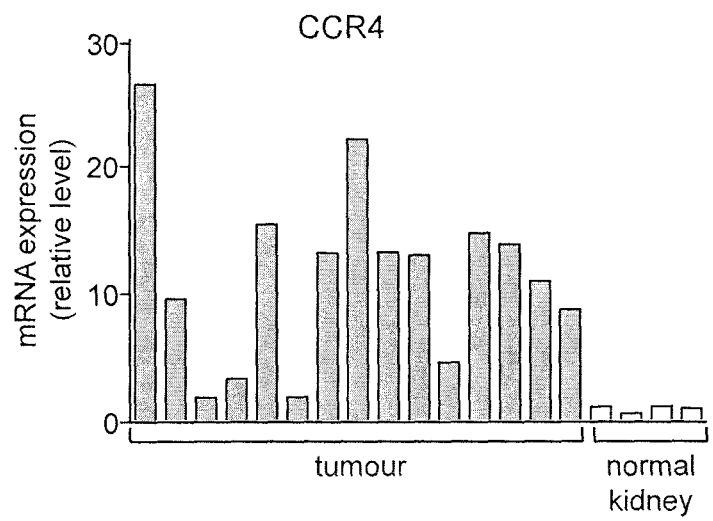

The present invention relates generally to methods of diagnosis, prognosis, stratification, and monitoring, in the field of cancer. The methods of the invention involve determining the ratio of chemokine thymus and activation-regulated chemokine (TARC), also known as CCL17, to macrophage-derived chemokine (MDC), also known as CCL22, in the blood or a blood component of a subject.

BACKGROUND

Cancer causes about 13% of all human deaths and the success of treatment is in many cases linked to the stage at which the cancer is diagnosed. There is therefore a need for better diagnostic and risk prediction (prognostic) tools for patients suffering from all types of cancer.

Chemokines play an important role inter alia in immune and inflammatory responses in various diseases, including cancer, viral infections, asthma and allergic diseases, as well as autoimmune pathologies such as rheumatoid arthritis and atherosclerosis. These small, secreted molecules are a growing superfamily of 8-14 kDa proteins characterised by a conserved four cysteine motif. The actions of chemokines are mediated by subfamilies of G protein-coupled receptors. Chemokines are divided into four different groups, CXC, CC, CX3C or C, depending on the position of the conserved cysteine residue, and receptor nomenclature essentially follows that of the chemokines. Thus, CC chemokines bind to CC chemokine receptors, CXC ligands bind to CXC receptors and so on.

Chemokine receptors and their ligands direct the trafficking of cells in normal tissue homeostasis and in disease, influencing cell motility, invasiveness and survival. In cancer, certain chemokines and their receptors are important for cell trafficking into and out of the tumour microenvironment. For instance, chemokines made by malignant and stromal cells can contribute to the extent and phenotype of the tumour-associated leukocyte component, to angiogenesis and to the generation of the fibroblast stroma. These stromal chemokines may also directly aid survival of the malignant cells. This is because malignant cells gain functional chemokine receptors that are not normally found on their normal counterparts. These receptors may contribute to metastatic activity; malignant cells become like leukocytes, able to respond to chemokine gradients at sites of metastasis.

Chemokine thymus and activation-regulated chemokine (TARC), also known as CCL17, displays chemotactic activity for T-lymphocytes, but not monocytes or granulocytes. It can specifically bind to chemokine receptor CCR4. In normal tissues, CCL17 is expressed by vascular and lymphatic endothelial cells, but is also produced by macrophages, dendritic cells and keratinocytes.

Macrophage-derived chemokine (MDC), also known as CCL22, can also specifically bind to chemokine receptor CCR4. CCL22 is generally considered to be a constitutively expressed chemokine, although it appears that its expression may also be modulated by certain stimuli. In normal tissues, CCL22 is a product of macrophages, monocytes, dendritic cells, B cells, and T cells. It is also found in epithelial tissues. For instance, intestinal epithelium constitutively produces CCL22 that can be further up-regulated by inflammatory cytokines such as TNF-α.

CCL17 and CCL22 are also found at increased levels at the site of tumours. Immunohistochemistry has revealed increased levels of CCL17 and CCL22 both at epithelial tumour cells and at cells that form the tumour stroma, for example in cervical cancer (WO2009037454).

Studies have demonstrated that the actions of chemokines are mediated by subfamilies of G protein-coupled receptors, among which is the receptor designated chemokine (C-C motif) receptor 4, or CC chemokine receptor 4 (CCR4). Specific ligands for CCR4 include CCL17 and CCL22.

CCR4 is believed to be important inter alia in the function of T cell chemotaxis and the migration of phagocytic cells to sites of inflammation. CCR4 is preferentially expressed on T-helper cell type 2 (Th2) cells and regulatory T (Treg) cells, whereas only limited expression on other healthy cells or tissues occurs.

CCR4 expression has also been detected in tumours. Tumours are a heterogeneous mixture of cells, being made up of inter alia neoplastic cells, fibroblasts, endothelial and immune-competent cells. Macrophages may represent up to 50% of tumour mass. Thus, tumours may include infiltrating immune cells, and these immune cells may express CCR4.

CCR4 is also expressed by certain neoplastic tumour cells. More specifically, CCR4 may be found not only in the tumour stroma, but it may expressed by epithelial tumour cells, i.e. neoplastic cells. Adult T cell leukaemia/lymphoma cells have long been known to express CCR4. More recently, CCR4 has also been found to be expressed by the neoplastic tumour cells of certain carcinomas (WO2009/037454 and WO2012/076883). CCR4 expression is believed to be an early event in carcinogenesis, particularly cancer of the cervix, oesophagus, kidney, brain, breast, ovary, prostate, stomach and pancreas. Thus, both haematological and non-haematological cancer cells, e.g. solid tumour cells, may express CCR4.

Various methods for the diagnosis, prognosis and/or monitoring of cancer exist, but there remains a need for further methods to advance the diagnosis, prognosis, monitoring and the like of cancer.

DESCRIPTION OF INVENTION

The present invention is predicated on an analysis of plasma levels of chemokines CCL17 and CCL22 in cancer patients. The inventors set out to determine whether plasma levels of either of these chemokines may be an indicator of progression-free survival or of overall survival of cancer patients. As shown in the Examples, neither CCL17 nor CCL22 alone was a useful indicator in this regard. However, the inventors surprisingly found that the ratio of CCL17 to CCL22 in plasma was a good indicator of progression-free survival and of overall survival. Within the group of patients analysed, those with higher ratios of CCL17:CCL22 had a decreased likelihood of progression-free survival and overall survival than those with lower ratios.

Figure 13:
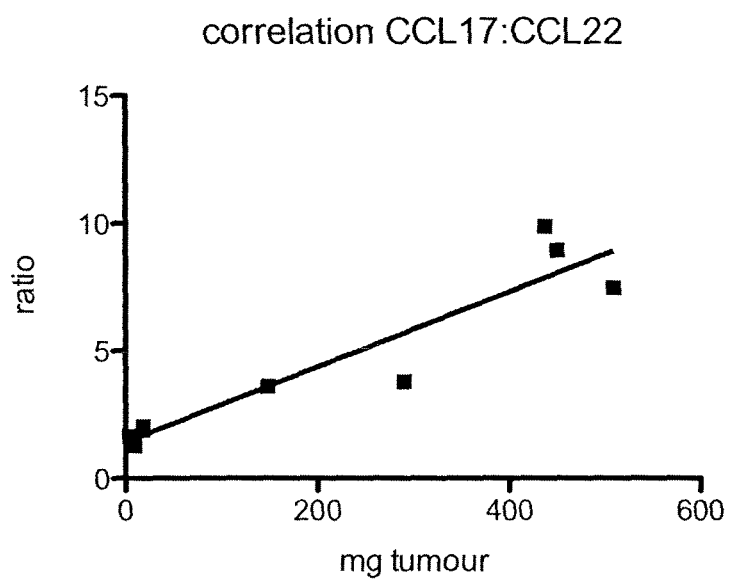

The inventors found that cancer patients typically have a higher ratio of plasma CCL17 to CCL22 than healthy subjects. Moreover, this ratio shows a clear correlation with tumour burden, as shown in FIG. 13, where there is a linear relationship between the ratio and tumour weight. The ratio is thus a marker of tumour burden, more particularly of the extent of the tumour burden, and of response to anti-cancer treatment, particularly anti-CCR4 treatment.

The inventors have determined that the ratio of circulating CCL17 to circulating CCL22 may be used to diagnose cancer, to monitor the development or progression of cancer, to make a prognosis, to predict response to treatment, to stratify patients to make decisions on treatment, and to monitor the response to anti-cancer treatment.

The "ratio of circulating CCL17 to circulating CCL22" is conveniently referred to herein simply as "the ratio".

Consequently, in one aspect the present invention provides the ratio of circulating CCL17 to circulating CCL22 as a diagnostic marker in cancer. The invention provides a method of obtaining information relevant to diagnosing cancer, comprising determining the ratio of circulating CCL17 to circulating CCL22 in a sample from a subject. More particularly, the invention provides a method of obtaining information relevant to diagnosing cancer, comprising determining the ratio of circulating CCL17 to circulating CCL22 in a sample from a subject and making a diagnosis as to whether the subject has cancer.

The method may optionally comprise comparing the ratio in said sample to a control ratio or a reference ratio. A diagnosis may be made by determining whether the subject's CCL17 to CCL22 ratio is higher or lower than a control or reference, i.e. whether it is increased.

A diagnosis may be made based solely on the ratio, or based on the ratio and one or more other diagnostic tools or markers. Thus, alternatively viewed there is provided a method of diagnosing cancer. Any of the method steps and features discussed herein in connection with a method of obtaining information relevant to a diagnosis apply mutatis mutandis to the method of diagnosis and vice versa. Thus, any statements herein referring to a "method of diagnosis" should be understood explicitly to be interchangeable with a "a method of obtaining information relevant to diagnosing cancer" and vice versa.

In a further aspect the present invention provides the ratio of circulating CCL17 to circulating CCL22 as a monitoring marker in cancer. The invention provides a method of obtaining information relevant to monitoring the development or progression of cancer, comprising determining the ratio of circulating CCL17 to circulating CCL22 in a sample from a subject. More particularly, the invention provides a method of obtaining information relevant to monitoring the development or progression of cancer, comprising determining the ratio of circulating CCL17 to circulating CCL22 in a sample from a subject and making a determination as to whether a cancer has developed or progressed.

The method may optionally comprise comparing the ratio in said sample to a control or reference ratio. A determination as to whether the cancer has developed or progressed may be made by determining whether the subject's CCL17 to CCL22 ratio is higher or lower than a control or reference, i.e. whether it is increased.

A determination as to whether the cancer has developed or progressed may be made based solely on the ratio, or based on the ratio and one or more other monitoring tools or markers. Thus, alternatively viewed there is provided a method of monitoring the onset or progression of cancer. Any of the method steps and features discussed herein in connection with a method of obtaining information relevant to monitoring apply mutatis mutandis to the method of monitoring and vice versa. Thus, any statements herein referring to a "method of monitoring" should be understood explicitly to be interchangeable with a "a method of obtaining information relevant to monitoring" and vice versa.

In a further aspect the present invention provides the ratio of circulating CCL17 to circulating CCL22 as a predictive marker in cancer. The invention provides a method of obtaining information relevant to predicting the likelihood of a cancer responding to treatment, comprising determining the ratio of circulating CCL17 to circulating CCL22 in a sample from a subject. More particularly, the invention provides a method of obtaining information relevant to predicting the likelihood of a cancer responding to treatment, comprising determining the ratio of circulating CCL17 to circulating CCL22 in a sample from a subject and predicting the likelihood of a cancer responding to treatment.

The method may optionally comprise comparing the ratio in said sample to a control or reference ratio. A prediction of the likelihood of a cancer responding to treatment may be made by determining whether the subject's CCL17 to CCL22 ratio is higher or lower than a control or reference, i.e. whether it is increased or decreased.

A prediction of the likelihood of a cancer responding to treatment may be made based solely on the ratio, or based on the ratio and one or more other predictive tools or markers. Thus, alternatively viewed there is provided a method of predicting the likelihood of a cancer responding to treatment. Any of the method steps and features discussed herein in connection with a method of obtaining information relevant to prediction apply mutatis mutandis to the method of predicting the likelihood of a cancer responding to treatment and vice versa. Thus, any statements herein referring to a "method of predicting" should be understood explicitly to be interchangeable with a "a method of obtaining information relevant to predicting" and vice versa.

In a further aspect the present invention provides the ratio of circulating CCL17 to circulating CCL22 as a stratification marker in cancer. The invention provides a method of obtaining information relevant to the stratification of subjects having cancer, preferably according to their need for treatment, comprising determining the ratio of circulating CCL17 to circulating CCL22 in a sample from a subject. More particularly, the invention provides a method of obtaining information relevant to the stratification of cancer patients, preferably according to their need for treatment, comprising determining the ratio of circulating CCL17 to circulating CCL22 in a sample from a subject and stratifying said subject, for example according to the subject's need for treatment.

The method may optionally comprise comparing the ratio in said sample to a control or reference ratio. A stratification may be made by determining whether the subject's CCL17 to CCL22 ratio is higher or lower than a control or reference, i.e. whether it is increased or decreased A stratification may be made based solely on the ratio, or based on the ratio and one or more other stratification tools or markers. Thus, alternatively viewed there is provided a method of stratification of subjects according to their likelihood of responding to treatment. Any of the method steps and features discussed herein in connection with a method of obtaining information relevant to stratification apply mutatis mutandis to the method of stratification and vice versa. Thus, any statements herein referring to a "method of stratification" should be understood explicitly to be interchangeable with a "a method of obtaining information relevant to the stratification" and vice versa.

In a further aspect the present invention provides the ratio of circulating CCL17 to circulating CCL22 as a prognostic marker in cancer. The invention provides a method of obtaining information relevant to cancer prognosis, comprising determining the ratio of circulating CCL17 to circulating CCL22 in a sample from a subject. More particularly, the invention provides a method of obtaining information relevant to cancer prognosis, comprising determining the ratio of circulating CCL17 to circulating CCL22 in a sample from a subject and making a cancer prognosis.

The method may optionally comprise comparing the ratio in said sample to a control or reference ratio. A prognosis may be made by determining whether the subject's CCL17 to CCL22 ratio is higher or lower than a control or reference, i.e. whether it is increased or decreased.

A prognosis may be made based solely on the ratio, or based on the ratio and one or more other monitoring tools or markers. Thus, alternatively viewed there is provided a method of prognosis. Any of the method steps and features discussed herein in connection with a method of obtaining information relevant to prognosis apply mutatis mutandis to the method of prognosis and vice versa. Thus, any statements herein referring to a "method of prognosis" should be understood explicitly to be interchangeable with a "a method of obtaining information relevant to prognosis" and vice versa.

In a further aspect the present invention provides the ratio of circulating CCL17 to circulating CCL22 as a marker of treatment response in cancer. The invention provides a method of obtaining information relevant to assessing/monitoring the response of a cancer to treatment, comprising determining the ratio of circulating CCL17 to circulating CCL22 in a sample from a subject. More particularly, the invention provides a method of obtaining information relevant to assessing/monitoring the response of a cancer to treatment, comprising determining the ratio of circulating CCL17 to circulating CCL22 in a sample from a subject and assessing/monitoring the response of a cancer to treatment.

The method may optionally comprise comparing the ratio in said sample to a control or reference ratio. An assessment/monitoring of the response of a cancer to treatment may be made by determining whether the subject's CCL17 to CCL22 ratio is higher or lower than a control or reference, i.e. whether it is increased or decreased.

An assessment/monitoring of the response of a cancer to treatment may be made based solely on the ratio, or based on the ratio and one or more other predictive tools or markers. Thus, alternatively viewed there is provided a method of assessing/monitoring the response of a cancer to treatment. Any of the method steps and features discussed herein in connection with a method of obtaining information relevant to assessment/monitoring of treatment response apply mutatis mutandis to the method of assessing/monitoring the response of a cancer to treatment and vice versa. Thus, any statements herein referring to a "method of assessing/monitoring" should be understood explicitly to be interchangeable with a "a method of obtaining information relevant to assessing/monitoring" and vice versa.

During therapy or subsequent to therapy, the monitoring methods of the present invention can be used to monitor the progress of cancer to assess the effectiveness of therapy or to monitor the progress of therapy, i.e. can be used for active monitoring of therapy. In such cases serial (periodic) determinations of the ratio for a change in said ratio will allow the assessment of whether or not, or the extent to which, cancer therapy has been effective, whether or not cancer is re-occurring or progressing in the subject and also the likely clinical outcome (prognosis) of the cancer should it re-occur or progress.

Equally, the methods of the present invention can be used in the active monitoring of patients which have not been subjected to therapy, e.g. to monitor the progress of the disease in untreated patients. Again serial measurements will allow an assessment of whether or not, or the extent to which, the cancer is progressing, thus, for example, allowing a more reasoned decision to be made as to whether therapeutic intervention is necessary or advisable.

Such monitoring can even be carried out on a healthy individual, for example an individual who is thought to be at risk of developing cancer, in order to obtain an early and ideally pre-clinical indication of cancer.

The skilled person will appreciate that any of the methods provided herein may be combined with one or more of the other methods provided herein and/or with one or more further methods.

For example, provided is a method which is a combination of two or more, e.g. three or more, four or more or five or more of the methods disclosed herein. Two or more of the diagnosis, prognosis, prediction, monitoring and/or stratification methods disclosed herein may be combined in any combination. When combining the methods, each method may be referred to as a step. The details provided herein regarding the methods of the invention apply mutatis mutandis to these steps.

Thus, provided is a method of assessing the onset and course of a cancer, said method including at least two steps selected from a step of diagnosing cancer, a step of monitoring the progression of cancer, a step of predicting the likelihood of cancer response to treatment, a step of stratification, a step of prognosis, and a step of monitoring response to treatment. Optionally, said method includes at least 3, 4, 5 or 6 of these steps. Optionally, any of these steps may be carried out more than once. For example, a step of monitoring the progression of cancer may be carried out both before and after treatment.

Optionally, any of the methods provided herein may also include a step of determining whether the subject or patient should receive an anti-cancer treatment, which is preferably an anti-CCR4 treatment. Particularly, if the method involves a determination that the subject has cancer, that a cancer has developed, that a cancer has progressed, that the prognosis is poor, that a cancer is likely to respond to anti-cancer treatment, and/or that a cancer has responded to treatment, then the method may include a step of determining that the subject or patient should receive an anti-cancer treatment, which is preferably an anti-CCR4 treatment.

Optionally, any of the methods provided herein may also include a step of determining, for a subject who is receiving, or has received, treatment, whether the treatment should be altered or ceased. For example, the method may include a step of determining that the treatment dose and/or frequency should be increased or decreased. In particular, if the method involves a determination that the ratio is increased, has increased over time, or has not decreased (or not decreased sufficiently) in response to a treatment, then the method may include a step of determining that the treatment dose and/or frequency should be increased. If the method involves a determination that the ratio is not increased, has decreased over time, or has decreased in response to a treatment, then the method may include a step of determining that the treatment dose and/or frequency should be decreased or that the treatment may be ceased.

The method may include a step of determining that a particular treatment should be replaced by another treatment, for example that one drug should be replaced with another drug. In particular, if the method involves a determination that the ratio is increased, has increased over time, or has not decreased (or not decreased sufficiently) in response to a treatment, then the method may include a step of determining that the treatment should be replaced by another treatment. If the method involves a determination that the ratio is not increased, has decreased over time, or has decreased in response to a treatment, then the method may include a step of determining that the treatment should not be replaced by another treatment.

Optionally, any of the methods provided herein may also include a step of administering an anti-cancer treatment, which is preferably an anti-CCR4 treatment, to said subject or patient. The method may then be referred to as a method of diagnosis and treatment; monitoring and treatment; prognosis and treatment; prediction and treatment; or stratification and treatment.

Optionally, any of the methods provided herein may be used in conjunction with any other known methods, particularly a known diagnostic, prognostic, predictive, and/or monitoring method for cancer.

One advantage of the methods of the present invention is that they allow for diagnosis, prognosis, prediction, stratification, and/or monitoring via a simple test for a biomarker ratio which can be quickly and easily carried out on a readily obtainable sample such as a blood sample.

In a further aspect the present invention provides a kit for use in any of the methods described herein. Also provided is the kit when used in any of these methods. Also provided is the use of said kit in any of the methods described herein.

Said kit comprises an agent suitable for determining the level of CCL17 and an agent suitable for determining the level of CCL22. Such an agent will typically have specific binding affinity for CCL17 or CCL22 respectively. Preferred agents are antibodies directed to CCL17 or CCL22 respectively. The kit may also comprise detection means, for example means to detect the agent suitable for determining the level of CCL17 or CCL22 respectively. In particular, said agent may be labelled with a detectable moiety, for example a fluorescent moiety.

The kit may also comprise sampling means.

A CCL17:CCL22 ratio which is increased, or high, is indicative of cancer. The higher the ratio, the higher the likelihood that the subject has cancer.

Thus, the method of diagnosis may involve a step of determining that the CCL17:CCL22 ratio is increased, or is high, and as a consequence of said determination diagnosing that the subject has cancer or has an increased likelihood of having cancer, or a step of determining that the CCL17:CCL22 ratio is not increased, or is low, and as a consequence of said determination diagnosing that the subject does not have cancer or has a decreased likelihood of having cancer.

The method of monitoring the development (onset) of cancer may involve a step of determining that the CCL17:CCL22 ratio is increased, or is high, and as a consequence of said determination determining or diagnosing that a cancer has developed or that there is an increased likelihood of a cancer having developed, or a step of determining that the CCL17:CCL22 ratio is not increased, or is low, and as a consequence of said determination determining or diagnosing that a cancer has not developed or that there is a decreased likelihood of a cancer having developed.

A CCL17:CCL22 ratio which is increased, or high, is indicative of the progression of cancer. The higher the ratio, the higher the likelihood that the cancer has progressed. Alternatively viewed, the higher the ratio, the more the cancer has progressed.

Thus, the method of monitoring the progression of cancer may involve a step of determining that the CCL17:CCL22 ratio is increased, or is high, and as a consequence of said determination determining or diagnosing that the cancer has progressed or has an increased likelihood of having progressed, or a step of determining that the CCL17:CCL22 ratio is not increased, or is low, and as a consequence of said determination determining or diagnosing that the cancer has not progressed or has an increased likelihood of not having progressed.

A CCL17:CCL22 ratio which is increased, or high, is indicative of an increased likelihood that the cancer patient has an adverse prognosis. Thus, the method of prognosis may involve a step of determining that the CCL17:CCL22 ratio is increased, or is high, and as a consequence of said determination determining that said patient has an adverse prognosis or an increased likelihood of an adverse prognosis, or determining that the CCL17:CCL22 ratio is not increased, or is low, and as a consequence of said determination determining that said patient does not have an adverse prognosis or has a decreased likelihood of an adverse prognosis.

The more the CCL17:CCL22 ratio is increased, i.e. the higher the ratio, the greater the likelihood that the cancer patient has an adverse prognosis. Thus, the method of prognosis may involve a step of determining the extent to which the CCL17:CCL22 ratio is increased and as a consequence of said determination determining the likelihood that the cancer patient has an adverse prognosis.

A CCL17:CCL22 ratio which increased, or high, is indicative of an increased likelihood that the cancer will respond to treatment. The higher the ratio, the higher the likelihood that the cancer will respond to treatment.

Thus, the method of prediction may involve a step of determining that the CCL17:CCL22 ratio is increased, or is high, and as a consequence of said determination determining that said cancer will respond to treatment or has an increased likelihood of responding to treatment, or determining that the CCL17:CCL22 ratio is not increased, or is low, and as a consequence of said determination determining that said cancer will not respond to treatment or has a decreased likelihood of responding to treatment.

Thus, the method of stratification may involve a step of determining that the CCL17:CCL22 ratio is increased, or is high, in one or more cancer patients and not increased, or low, in one or more other cancer patients and as a consequence of said determination stratifying said patients having an increased, or high, ratio into a first group having an increased likelihood of requiring, benefitting from and/or responding to treatment and stratifying said patients not having an increased ratio, or having a low ratio, into a second group having a decreased likelihood of requiring, benefitting from and/or responding to treatment.

A CCL17:CCL22 ratio which decreased, or low, after treatment is indicative of an increased likelihood that the cancer has responded to said treatment. The lower the ratio, the higher the likelihood that the cancer has responded to said treatment Thus, the method of assessing/monitoring the response to treatment may involve a step of determining that the CCL17:CCL22 ratio is decreased, or is low, and as a consequence of said determination determining that the cancer has responded to said treatment, or has an increased likelihood of having responded to said treatment, or a step of determining that the CCL17:CCL22 ratio is not decreased, or is high, and as a consequence of said determination determining that the cancer has not responded to said treatment, or has an increased likelihood of not having responded to said treatment.

Alternatively viewed, the extent to which the CCL17:CCL22 ratio is decreased after treatment is indicative of the extent to which the cancer has responded to said treatment. The greater the decrease in the ratio, the greater the response to treatment. Thus, the method of assessing/monitoring the response to treatment may involve a step of determining to what extent the CCL17:CCL22 ratio is decreased and as a consequence of said determination determining to what extent the cancer has responded to said treatment.

An "increase" in the ratio or an "increased" or "higher" ratio as described herein includes any measurable increase or elevation of the ratio when the ratio is compared with a control or reference. A "decrease" in the ratio or a "decreased" or "lower" ratio as described herein includes any measurable decrease of the ratio when the ratio is compared with a control or reference.

A "high" ratio is a ratio which is higher than a control or reference and a "low" ratio is a ratio which is lower than a control or reference.

As mentioned above, in some embodiments, any of the methods of the inventions may optionally comprise comparing the ratio to a control ratio or to a reference ratio.

The term "control" ratio is used herein to refer to the ratio of a healthy, i.e. non-cancerous control. In some embodiments, the control may be a "self" control, i.e. a ratio determined for said (test) subject at an earlier time point. In some embodiments, the control ratio is based on one or more subjects other than the test subject.

The term "reference" ratio is used herein to refer to the ratio of a cancerous control. The reference may be a "self" reference, i.e. a ratio determined for said subject at an earlier time point. In some embodiments, the reference ratio is based on one or more subjects other than the test subject.

Typically, the control ratio would be determined by determining individual ratios in a suitable set of healthy subjects and determining the median or mean of said ratios. Alternatively, a single ratio determined in a healthy subject may be used as the control. The healthy subject may be the test subject at an earlier time point, in which case the control may be denoted a "self" control, or it may be a different subject, i.e. not the test subject.

Typically, the reference ratio would be determined by determining individual ratios in a suitable set of cancerous subjects and determining the median or mean of said ratios. However, particularly in the context of monitoring the progression of cancer or assessing/monitoring the response to treatment, the reference ratio is preferably a "self" reference, i.e. a ratio determined for said test subject at an earlier time point.

It should be noted that although the control ratio or the reference ratio for comparison may be derived by testing an appropriate control/reference subject, or a set of control/reference subjects, the methods of the invention would not necessarily involve carrying out active tests on such a control/reference subject or a set of control/reference subjects. Instead, they may involve a comparison with a control/reference ratio which had been determined previously from a control/reference subject or from a set of control/reference subjects.

Appropriate control subjects or samples for use in the methods of the invention would be readily identified by a person skilled in the art. Such subjects might also be referred to as "normal" subjects. Examples of appropriate control subjects would include healthy subjects, for example individuals who are not suffering from cancer. Preferably, they also have no history of any form of cancer. Preferably, they also have no other concurrent disease. Preferably control subjects are not regular users of any medication.

Appropriate reference subjects or samples for use in the methods of the invention would be readily identified by a person skilled in the art. Such subjects would include individuals who have cancer. Preferably, the reference subjects have the same form of cancer as the test subject, so if the test subject has renal cancer, the reference subjects are preferably subjects who have renal cancer, whereas for a test subject having pancreatic cancer, the reference subjects are preferably subjects who have pancreatic cancer and so on. Preferably, the reference subjects also have an equivalent stage of cancer, i.e. for a test subject having early stage cancer the reference subjects should ideally have early stage cancer, whereas for a test subject having late stage cancer the reference subjects should ideally have last stage cancer. Preferably, the cancer of the reference subjects has not metastasised. The skilled person can readily determine whether the test subject and control or reference subjects should be matched for other criteria. For example, optionally the control or reference subject(s) may match the test subject with respect to one or more of the following criteria: age, race, and/or sex.

Preferably the ratio in question is determined by analysing a test sample which is obtained from or removed from said patient by an appropriate means. The determination is thus preferably carried out in vitro.

As will be clear from the discussions herein, the methods of the present invention can involve single or one off measurements or determinations of the ratio in respect of a subject, or may involve multiple measurements or determinations over a period of time, e.g. for the ongoing monitoring of the progression of cancer.

The control or reference ratio may be a discrete figure or a range.

As mentioned above, the methods of the invention may involve a determination as to whether the ratio is increased or decreased. This can be expressed in relative or absolute terms.

In relative terms the ratio is increased when it is above a predetermined threshold, i.e. a cut-off, when compared to the control or reference. A patient is considered to have an increased ratio if the ratio rises above the cut-off. For example, at its simplest, if the assessment is to be made based on a comparison with a control or reference, an increased ratio may be at least 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10, 11, 12, 13, or 14 times higher than the control or reference ratio.

In other words the cut-off for "increased" can be defined as least 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10, 11, 12, 13, or 14 times higher than the control ratio.

Alternatively, the cut-off for an "increased" ratio can be defined by the lower bound of 3, 2.5, 2.4, 2.3, 2.2, 2.1, 2, 1.9, 1.8, 1.7, 1.6, 1.5, 1, 0.8, 0.5 or 0.3 standard deviations from the mean ratio or median ratio in the control or reference samples. The mean, median and standard deviation are determined by standard statistical analysis.

A determination can alternatively be made based on absolute values of the ratio, as is set out in more detail below. It must be appreciated that the type of sample in which the ratio is determined will determine which absolute values should be used as a control or reference. In particular, as can be seen from comparing FIG. 12 to FIG. 16, an analysis of serum samples may be expected to yield higher ratios than an analysis of plasma samples. For example, it would appear that in mice, the serum ratio is about one order of magnitude higher than the plasma ratio. The following values are provided based on data obtained with plasma samples, so these values are examples of values appropriate to use when determining the ratio is a plasma sample.

A control ratio may, for example, be about 0.001-0.4 or any value that falls within this range. Preferably, the control ratio is about 0.001-0.35, about 0.001-0.3, about 0.001-0.2.5 or about 0.001-0.2, e.g. 0.19 or less, 0.18 or less, 0.17 or less, 0.16 or less, 0.15 or less, 0.14 or less, 0.13 or less, 0.12 or less, 0.11 or less, 0.10 or less, 0.09 or less, 0.08 or less, 0.07 or less, 0.06 or less, 0.05 or less, 0.04 or less, or 0.03 or less.

A reference ratio may, for example, be about 0.6 or less, but above 0.05. Thus, when expressed as a range or absolute values, the reference ratio may, for example, have an upper limit of about 0.6, 0.55, 0.5, 0.49, 0.48, 0.46, 0.44, 0.42, 0.4, 0.38, 0.37, 0.36, 0.35, 0.34, 0.33, 0.32, 0.31, 0.3, 0.29, 0.28, 0.27, 0.26, 0.25, 0.24, 0.23, 0.22, 0.21. 0.2, 0.19, 0.18, 0.17, 0.16, 0.15, 0.14, 0.13, 0.12, 0.11 or 0.1 and a lower limit of about 0.05, 0.08, 0.1, 0.12, 0.14, 0.16, 0.18, 0.2, 0.21, 0.22, 0.23, 0.24, 0.25, 0.26, 0.27, 0.28, 0.29 or 0.3. Any of these upper limits may be combined with any of these lower limits, provided that the lower limit is lower than the selected upper limit.

For renal cancer, particularly advanced renal cancer, the reference ratio is preferably about 0.5-0.2, e.g. 0.45-0.25, or 0.4-0.28, preferably about 0.32-0.35. For ovarian cancer, preferably HGS ovarian cancer, the reference ratio is preferably about 0.2-0.08, e.g. a range having an upper limit of about 0.19, 0.18, 0.17, 0.16, 0.15, 0.14, 0.13, 0.12, 0.11 or 0.1, and a lower limit of about 0.08. For pancreatic cancer, the reference ratio is preferably about 0.36-0.11 e.g. a range having an upper limit of about 0.36, 0.35, 0.34, 0.33, 0.32, 0.31, 0.3, 0.29, 0.28, 0.27, 0.26, 0.25, 0.24, 0.23, 0.22, 0.21. 0.2, 0.19, 0.18, 0.17, 0.16, 0.15, 0.14 or 0.13, and a lower limit of about 0.11.

These values thus may provide the cut off level, i.e. the ratio is increased if it is above these values. All of the absolute values listed above are provided based on an analysis of the ratio in plasma samples. It is believed that higher absolute values would be appropriate when analysing serum samples. For example, for serum samples, each of the values provided above may be multiplied by 10, 9, 8, 7, 6, 5, 4, 3 or 2.

As is apparent from the discussion herein, whilst some of the methods of the invention may use the same control or reference ratio as other methods, not every control or reference may be appropriate for every method. The skilled person will be able to determine what control or reference ratio should be used, but the following are examples of particularly appropriate controls and references.

For the method of diagnosis, it is particularly appropriate to use a control ratio, optionally a self control ratio.

For the method of monitoring the onset, it is particularly appropriate to use a control ratio, preferably a self control ratio.

For the method of monitoring the progression of cancer, it is particularly appropriate to use a self reference ratio, although alternatively a reference ratio may be used, or a control ratio may be used, which may be a self-control.

For the method of prognosis, it is particularly appropriate to use a reference ratio, although alternatively a control ratio may be used.

For the method of prediction or stratification, it is particularly appropriate to use a reference ratio, although alternatively a control ratio may be used.

For the method of assessing/monitoring the response to treatment, it is particularly appropriate to use a reference ratio, preferably a self reference ratio, although alternatively a control ratio may be used.

The skilled person will appreciate that the analysis of the ratio will depend on the control or reference used. Thus, in the method of prognosis, the ratio will typically be compared to a reference ratio and consequently a ratio which is higher than the reference is indicative of a poor/worse prognosis and a ratio which is lower than the ratio is indicative of a good/better prognosis. The ratio may alternatively be compared to a control ratio, in which case a ratio which is lower than, equal to, similar to, or only increased by a small factor compared to the control ratio is indicative of a good/better prognosis and a ratio which is increased by a large factor compared to the control ratio is indicative of a poor/worse prognosis.

It follows that for the method of prediction or stratification the ratio will typically be compared to a reference ratio and consequently a ratio which is higher than the reference is indicative of a cancer likely to respond to treatment and a ratio which is lower than the reference is indicative of a cancer less likely to respond to treatment. The ratio may alternatively be compared to a control ratio, in which case a ratio which is lower than, equal to, similar to, or only increased by a small factor compared to the control ratio is indicative of a cancer unlikely or less likely to respond to treatment and a ratio which is increased by a large factor compared to the control ratio is indicative of a cancer likely or more likely to respond to treatment.

For the method of assessing/monitoring the response to treatment the ratio will typically be compared to a reference ratio and consequently a ratio which is lower than the reference is indicative of a cancer which has responded to treatment. The ratio may alternatively be compared to a control ratio, in which case a ratio which is lower than, equal to, similar to, or only increased by a small factor compared to the control ratio is indicative of a cancer which has responded (well) to treatment and a ratio which is increased by a large factor compared to the control ratio is indicative of a cancer which has not responded or which has responded less well to treatment.

Optionally, any of the methods of the invention, particularly the method of monitoring the progression of cancer or the method of assessing/monitoring the response to treatment may comprise determining the ratio of circulating CCL17 to circulating CCL22 from a cancer patient periodically.

By "periodically" is meant that determinations are made at two or more, e.g. at least 2, 3, 4, 5, 6, 7, 8, 9 or 10 different time points. The determinations may be made at regular or irregular intervals. The intervals may be 1, 2, 3, 4, 5, 6, 7, 8, 9 or 10 days, weeks, months or years. The ratio determined at any given time point may be compared to one or more earlier values to determine whether an increase or decrease in the ratio has occurred.

An increase in the ratio compared to an earlier time point is indicative of the cancer having progressed; no significant changes in the ratio over time is indicative of a lack of cancer progression; and a decrease in the ratio compared to an earlier time point is indicative of the cancer having regressed.

Thus, the method of monitoring the progression of cancer may involve a step of determining that the cancer has progressed if the ratio at a first time point is lower than the ratio at a later (second or subsequent) time point, or a step of determining that the cancer has not progressed, i.e. is progression-free, if the ratio at a first time point is substantially the same as the ratio at a later (second or subsequent) time point, or a step of determining that the cancer has regressed if the ratio at a first time point is higher than the ratio at a later (second or subsequent) time point.

The term "diagnosis" or "diagnosing" as used herein refers to the determination whether or not a patient is suffering from a disease.

The term "monitoring" as used herein refers to the determination whether any changes take place/have taken place. Typically, it is determined whether any changes have taken place over time, i.e. since a previous time point. The change may, for example, be the development and/or progression of a disease, such as cancer.

The term "prognosis" as used herein refers to risk prediction of the severity of disease or of the probable course and clinical outcome associated with a disease. Thus, the term "method of prognosis" as used herein refers to methods by which the skilled person can estimate and/or determine a probability that a given outcome will occur. The outcome to which the prognosis relates may be morbidity and/or mortality. In particular, the prognosis may relate to "progression-free survival" (PFS), which is the length of time that a patient lives with the disease without the disease progressing. Thus, PFS may be the time from the start of therapy to the date of cancer progression, or the time from the end of therapy to the date of cancer progression.

By "progressing" or "progression" is meant that the disease gets worse, i.e. that the severity increases, for example that the tumour burden increases, for example a tumour increases in size and/or weight, that the cancer becomes malignant or more malignant, and/or that metastasis develops or the incidence and/or rate of metastasis increases.

The prognosis may relate to overall survival. By "overall survival" (OS) is meant the length of time that a patient lives with the disease before death occurs. Overall survival may, for example, be defined as the time from diagnosis of the cancer, treatment start, or treatment completion, until death. Overall survival is typically expressed as an "overall survival rate", which is the percentage of people in a study or treatment group who are still alive for a certain period of time after they were diagnosed with, or started treatment for, or completed treatment for, a disease, such as cancer. The overall survival rate may, for example, be stated as a five-year survival rate, which is the percentage of people in a study or treatment group who are alive five years after their diagnosis or the start or completion of treatment.

Statistical information regarding the average (e.g. median, mean or mode) OS and PFS of patients having a particular type of cancer is available to those skilled in the art. A determination whether a subject has, or is likely to have, an increased or decreased OS or PFS compared to such an average may therefore be made.

A determination that the likelihood and/or length of PFS and/or overall survival is decreased means that the prognosis is poor or adverse. The terms "poor" and "adverse" are used interchangeably herein. A "poor" prognosis may be defined as a prognosis that is worse than the reference prognosis for a patient, so it may also be referred to as a "worse" prognosis, and a "good" or "non-adverse" prognosis may be defined as a prognosis that is better than the reference prognosis for a patient so it may also be referred to as a "better" prognosis. The skilled person will appreciate that for the "reference prognosis" patients having the same type of cancer, preferably the same stage of cancer, should be used. The "reference prognosis" may be the average prognosis or a typical prognosis determined by any other suitable method.

An adverse or worse prognosis may be defined as a shorter overall survival or an increased likelihood of shorter overall survival and/or shorter PFS or an increased likelihood of shorter PFS.

By "regressing" or "regression" is meant that the disease improves, i.e. that the severity decreases, for example that the tumour burden decreases, for example a tumour decreases in size and/or weight or becomes undetectable, that the cancer becomes less malignant, and/or that the incidence and/or rate of metastasis decreases.

A response to treatment may include progression, regression, a combination of progressive and regressive elements, or the absence of any progression or regression. Thus, a response to treatment may include a change in one or more criteria selected from tumour size, tumour weight, tumour number, malignancy and metastasis. Which changes constitute progression or regression is discussed elsewhere herein.

By "development" is meant the onset of a disease.

The term "prediction" or "predicting" as used herein refers to determining the likelihood of a particular outcome.

The term "stratification" or "stratifying" as used herein refers to the division of a population into subpopulations on the basis of specified criteria. More particularly, it refers to the division of a cohort of subjects or patients into at least two groups on the basis of specific criteria, which in the context of the present invention comprise or consist of the ratio.

The term "treatment" or "treating" as used herein refers to a course of action which is aimed at bringing about a medical benefit for a subject. The treatment may be prophylactic or therapeutic; preferably, it is therapeutic.

By "prophylactic" is meant that the treatment is preventative, i.e. it is applied before the onset of disease. By "therapeutic" is meant that the treatment is applied after the onset of disease.

The treatment is preferably an anti-cancer treatment. Reference herein to "anti-cancer treatment" includes any treatment directed at treating cancer. The treatment may involve surgery, radiation and/or drugs. Drug treatment is preferred. This may involve chemotherapy.

In some embodiments, the anti-cancer treatment is an anti-CCR4 treatment. Thus, any reference herein to "treatment" should be understood to be preferably an anti-CCR4 treatment.

By "anti-CCR4" treatment is meant any treatment which directly or indirectly lowers or inhibits the level and/or activity of CCR4. The inhibition may be partial or complete. Preferably, the anti-CCR4 treatment directly inhibits the activity of CCR4, most preferably by interacting directly with CCR4. Thus, the treatment may involve an agent which prevents CCR4 from being activated by one or more of its ligands, particularly CCL17 and/or CCL22. Preferably, CCR4 is prevented from being activated by any of its ligands. For example, the agent may block CCR4 from binding one or more of its ligands, preferably CCL17 and/or CCL22, and thereby prevent any activation that the binding would normally cause.

The agent may, for example, be an antibody which specifically binds to CCR4, or a chemical molecule which is a CCR4 antagonist. Examples of chemical CCR4 antagonists include organic chemical molecules having anti-CCR4 activity, examples of which include sulphonamide compounds, pyrido[2,3-d]pyrimidine derivatives, 2-aminothiazole derivatives, 2-aminoquinazolines and piperazines. Suitable antibodies and chemical antagonists are well known in the art and examples are disclosed inter alia in WO2010/142952, WO04108717 and WO02094264.

In some embodiments, the anti-CCR4 treatment affects CCR4 activity by interacting directly with a ligand of CCR4, preferably CCL17 and/or CCL22. Thus, the treatment may involve an agent which binds specifically to CCL17 or CCL22 and preferably blocks said chemokine from activating CCR4. The agent may, for example, be an antibody which specifically binds to CCL17 or CCL22, or a chemical molecule which is a CCL17 or CCL22 antagonist.

The ratio of circulating CCL17 to circulating CCL22 may be determined by dividing the level of CCL17 by the level of CCL22. These levels may have been predetermined, but in some embodiments of any of the methods of the invention the method may include a step of measuring the levels of circulating CCL17 and the levels of circulating CCL22. The measurement may be carried out in vivo, but preferably it is carried out in vitro on a provided sample from the patient.

Preferably, the ratio of CCL17 protein to CCL22 protein is determined, so these chemokines are measured at the protein level. Such measurement may be made by any appropriate means, a number of which are well known and documented in the art. For example, antibodies may be used. Antibodies specific for CCL17 and CCL22 respectively are well known in the art and are commercially available, for example from AbD Serotec (4350 Lassiter at North Hills Avenue, Suite 250, Raleigh, N.C. 27609) or LifeSpan Biosciences, Inc. (2401 Fourth Avenue, Suite 900, Seattle, Wash. 98121);

Examples of methods which may be used to detect protein levels of CCL17 and/or CCL22 include immunoassays such as a radioimmunoassay (RIA) or fluorescence immunoassay, immunoprecipitation and immunoblotting or Enzyme-Linked ImmunoSorbent Assay (ELISA), with RIA and/or ELISA normally being the method of choice.

Both ELISA- and RIA-based methods can be carried out by methods which are standard in the art and would be well known to a skilled person. Such methods generally involve the use of an antibody to the chemokine to be detected, which is incubated with the sample to allow detection of the chemokine in the sample. Any appropriate antibodies can be used and examples of these are described elsewhere herein and in the prior art. For example, appropriate antibodies to CCL17 or CCL22, or antibodies which recognise particular epitopes thereof, can be prepared by standard techniques, e.g. by immunization of experimental animals. The same antibodies can generally be used to detect the chemokine in any immunoassay (e.g. a RIA-based assay or an ELISA-based assay), with the appropriate modifications made to the antibodies in terms of labelling etc.

A particularly suitable assay for determining the levels of CCL17 and CCL22 is an immunoassay system which is available from Meso Scale Discovery (1601 Research Boulevard, Rockville, Md. 20850-3173, USA).

Meso Scale Discovery™ (MSD)'s multi-array technology is a multiplex immunoassay system that enables the measurement of biomarkers utilizing electrochemiluminescent detection. In an MSD assay, specific Capture Antibodies for the analytes are coated in arrays in each well of a 96-well carbon electrode plate surface. The detection system uses SULFO-TAG™ labels that emit light upon electrochemical stimulation initiated at the electrode surfaces of the MULTI-ARRAY™ and MULTI-SPOT™ plates. The electrical stimulation is decoupled from the output signal, which is light, to generate assays with minimal background. MSD labels can be conveniently conjugated to biological molecules, are stable and are non-radioactive. Additionally, only labels near the electrode surface are detected, enabling non-washed assays. Further details of this assay may be found in the company's literature. The skilled person may, of course, use appropriate equivalent immunoassays provided by other suppliers.

In the methods of the invention, the amount of CCL17 and/or CCL22 may be determined by contacting a blood or blood component sample from said patient with an antibody that binds to the chemokine to be detected, subjecting the sample and the antibody to conditions which allow the antibody to bind and determining the amount of said chemokine in said sample.

The methods of the invention are concerned with the "circulating" levels of these chemokines. The term "circulating" is used herein to signify the circulation, i.e. the blood stream, which may be contrasted with localised levels of these chemokines. In particular, the present invention is not concerned with the levels of CCL17 or CCL22 within the tumour or the tumour microenvironment.

Circulating levels of these chemokines may be determined in a suitable sample of blood or a blood component or derivative such as plasma or serum. Plasma is particularly preferred. Thus, any reference herein to "circulating" levels should be understood to mean preferably the levels in the blood, plasma or serum. If plasma (or some other blood component) is the sample to be analysed, then prior to the assay, plasma (or the other blood component) can be separated from a blood sample by methods well known and documented in the art.

The methods of the invention may optionally further comprise a step of obtaining a sample from the patient, for example a step of obtaining a blood sample. However, preferable the methods are carried out on a provided sample.

The methods of the invention concern cancer. "Cancer" is a collective term for conditions characterised by neoplasia, i.e. the abnormal growth or division of cells. Cancerous cells may thus be referred to as "neoplastic". A collection of cancer cells is often referred to as a "tumour" and the terms "tumour" and "cancer" may be used interchangeably.

The cancer may be any cancer, such as carcinomas, sarcomas, leukaemias, lymphomas and gliomas. Preferably, the cancer is a carcinoma, sarcoma and/or glioma, most preferably a carcinoma. The cancer may be benign or malignant. Preferably, it is malignant.

Examples of suitable cancers include, without limitation, kidney cancer, ovarian cancer, pancreatic cancer, oesophagus cancer, cervical cancer, uterine cancer, bladder cancer, gallbladder cancer, liver cancer, head and neck cancer, squamous cell carcinoma, gastrointestinal cancer, breast cancer, prostate cancer, testicular cancer, lung cancer, non-small cell lung cancer, non-Hodgkin's lymphoma, Hodgkin's lymphoma, multiple myeloma, leukemia, adult T cell leukaemia, laryngeal cancer, brain cancer, neuroblastoma, stomach cancer, endometrial cancer and melanoma. Kidney (renal), ovarian and pancreatic cancer are preferred, kidney cancer being particularly preferred. In some embodiments, the cancer excludes colorectal cancer.

Certain cancers express CCR4, either at substantially the same level as the corresponding healthy tissue, or at increased levels. By this is meant that it is the neoplastic cells that express CCR4. In some embodiments, the cancer is a cancer which expresses CCR4, preferably at increased levels compared to healthy tissue. As mentioned above, in addition to neoplastic cells, tumours may include infiltrating cells, which may express CCR4, so in some embodiments, the cancer presents as a tumour which includes CCR4-expressing non-neoplastic cells. The tumour stroma may include CCR4-expressing cells, so in some embodiments, the cancer presents as a tumour which includes CCR4- expressing stromal cells. In some embodiments, one or more of the above may be combined, so the tumour may include CCR4-expressing neoplastic cells, CCR4-expressing non-neoplastic cells and/or have a stroma which includes CCR4-expressing stromal cells.

The methods of the invention may be carried out on a subject who has cancer or a subject who does not have cancer. The subject may be suspected of having cancer or the subject may not be suspected of having cancer. The subject may be confirmed as having cancer. The subject may be symptomatic or asymptomatic with regard to cancer. A subject who is receiving medical attention may be referred to as a "patient". Any reference herein to a "subject" should therefore be understood to include reference to a patient.

For example, the method may be carried out as part of a screening programme. The method may also be carried out to confirm the results of a different method, for example to confirm whether a subject has cancer, whether cancer has developed, whether cancer has progressed, whether the prognosis is good or bad, whether the subject should receive treatment, whether the cancer is likely to respond to treatment and/or whether the cancer has responded to treatment.

The methods of the invention as described herein can be carried out on any subject which may suffer from cancer. The methods are generally carried out on mammals, for example humans, other primates such as monkeys, laboratory mammals, e.g. mice, rats, rabbits, guinea pigs, livestock mammals, e.g. horses, cattle, sheep, pigs, or domestic pets, e.g. cats, dogs. In preferred embodiments the mammals are humans. However, in other embodiments, the ratio can be used as cancer markers in any appropriate animal model.

The invention will now be described in more detail by reference to the following non-limiting Figures, Tables and Examples.

Tables:

Table 1 shows data generated by the inventors concerning the CCL17:CCL22 ratio in plasma samples of renal cancer patients and pancreatic cancer patients compared to healthy controls. The patients groups and the normals (control) group all included male and female subjects.

Table 2 shows data generated by the inventors concerning the CCL17:CCL22 ratio in plasma samples of high grade serous (HGS) ovarian cancer patients compared to healthy controls. Ovarian cancer only affects females, so the patients group and the normals (control) group only included female subjects.

TABLE 1

CCL17:CCL22 ratio in renal cancer (RCC) patients and pancreatic cancer patients compared to normals (healthy controls)

| CCL17:CCL22 human | RCC | Pancreatic | Normal |
| --- | --- | --- | --- |
| Number of values | 47 | 11 | 26 |
| Minimum | 0.04943 | 0 | 0.006997 |
| 25% Percentile | 0.2005 | 0.1142 | 0.02599 |
| Median | 0.3394 | 0.2526 | 0.05399 |
| 75% Percentile | 0.5552 | 0.3621 | 0.1202 |
| Maximum | 1.232 | 0.5059 | 0.3979 |
| Mean | 0.4189 | 0.256 | 0.09147 |
| Std. Deviation | 0.2868 | 0.1475 | 0.1 |
| Std. Error | 0.04184 | 0.04447 | 0.01961 |
| Lower 95% CI of mean | 0.3347 | 0.1569 | 0.05108 |
| Upper 95% CI of mean | 0.5031 | 0.3551 | 0.1319 |
| Sum | 19.69 | 2.816 | 2.378 |

TABLE 2

CCL17:CCL22 ratio in HGS ovarian cancer patients compared to normals (healthy controls, females only)

| | HGS | Normals |
| --- | --- | --- |
| Number of values | 23 | 10 |
| Minimum | 0.05523 | 0.006997 |
| 25% Percentile | 0.0887 | 0.01455 |
| Median | 0.1266 | 0.03194 |
| 75% Percentile | 0.2083 | 0.08219 |
| Maximum | 0.7885 | 0.2778 |
| Mean | 0.1996 | 0.06297 |
| Std. Deviation | 0.1909 | 0.08324 |
| Std. Error | 0.03981 | 0.02632 |
| Lower 95% CI of mean | 0.1171 | 0.003419 |
| Upper 95% CI of mean | 0.2822 | 0.1225 |
| Sum | 4.592 | 0.6297 |

FIGURES

FIG. 1 Bar chart showing results of Example 1. CCR4 mRNA was measured by real-time RT-PCR in samples from renal cancer biopsies and compared with samples from normal kidney. CCR4 mRNA expression levels are shown as relative to expression levels of a housekeeping gene (the 18S gene).

Figure 2:
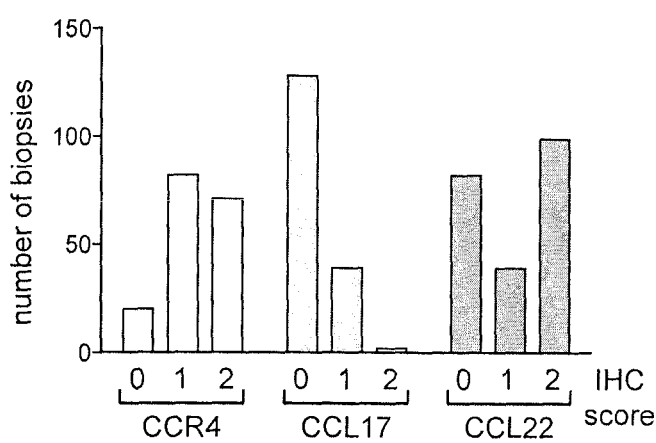

FIG. 2 Bar chart showing results of Example 1. Levels of CCR4 and its ligands CCL17 and CCL22 were analysed by immunohistochemistry (IHC) in a tissue microarray (TMA) of renal cancer biopsies from human patients. Each biopsy was scored 0—no staining, 1—weak staining, 2—strong staining for CCR4, CCL17 or CCL22 respectively.

Figure 3:
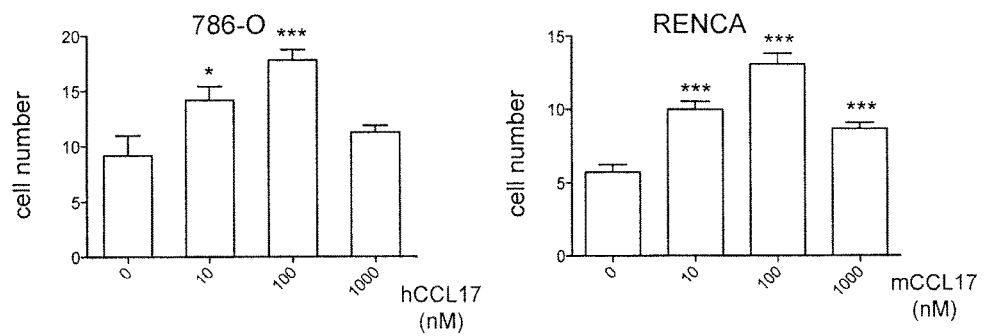

FIG. 3 Bar chart showing results of Example 1. 786-O (human renal carcinoma cell line) and RENCA (murine renal cancer cell line) response to different concentrations of human and murine CCL17, respectively, was analysed in a Transwell-based migration assay over 16 hours. Cell number/field (40× magnification) is indicated. The average of three experiments is shown. Asterisks represent a p value of *=p≤0.05, =p≤0.01, and *=p≤0.001, respectively.

Figure 4:
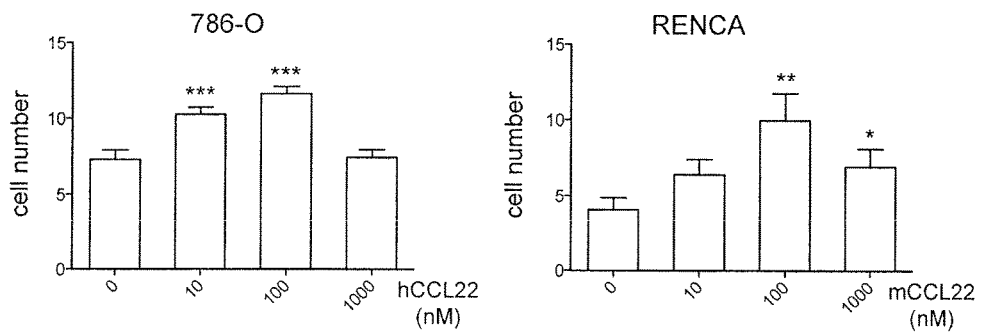

FIG. 4 Bar chart showing results of Example 1. 786-O and RENCA cell line response to different concentrations of human and murine CCL22, respectively, was analysed in a Transwell-based migration assay over 16 hours. Cell number/field (40× magnification) is indicated. The average of three experiments is shown. Asterisks represent a p value of *=p≤0.05, =p≤0.01, and *=p≤0.001, respectively.

Figure 5:
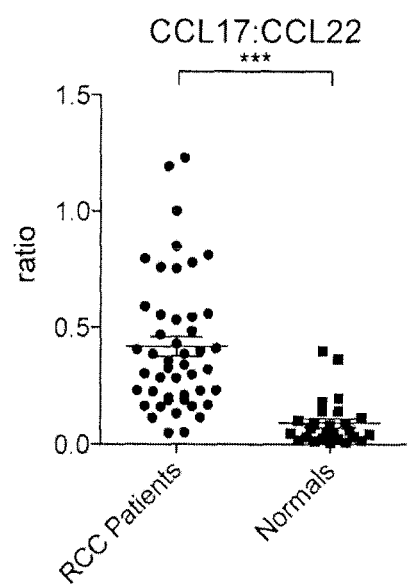

FIG. 5 Graph showing results of Example 2. The mean ratio of plasma CCL17:CCL22 in renal cancer patients is significantly higher than the mean ratio of plasma CCL17:CCL22 in normal (healthy) controls. Asterisks represent a p value of ***=p≤0.001.

Figure 6:
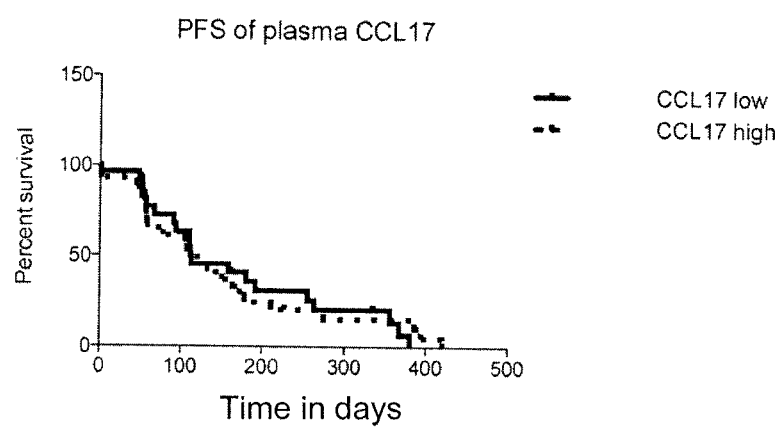
Figure 6:
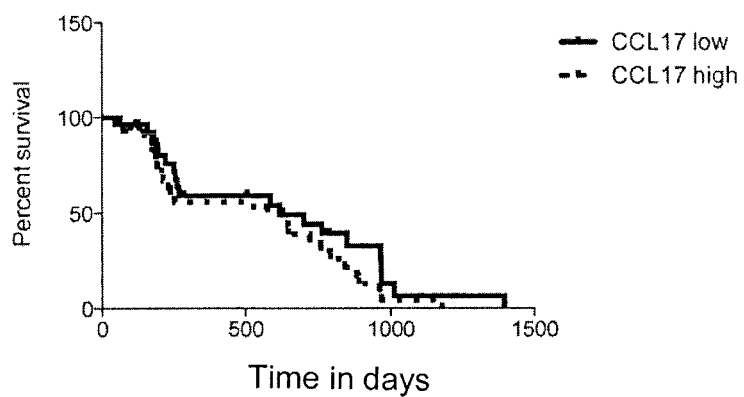

FIG. 6 Graph showing results of Example 2. Part A) shows progression-free survival (PFS) and part B) shows overall survival plotted against time in days. The graph compares the outcome for patients with high CCL17 to the outcome for patients with low CCL17. The y-axis shows time in days.

Figure 7:
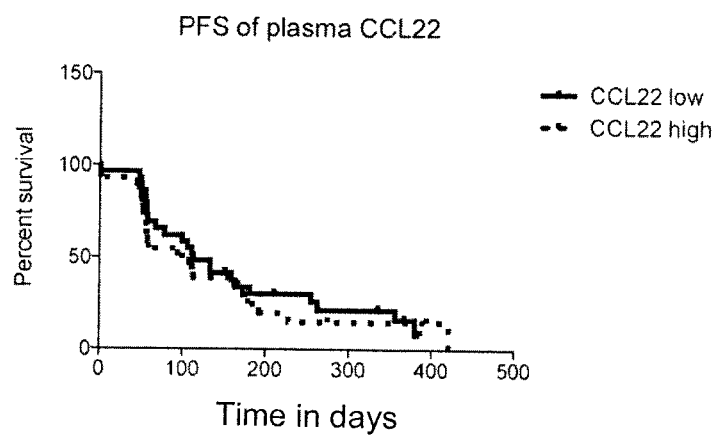
Figure 7:
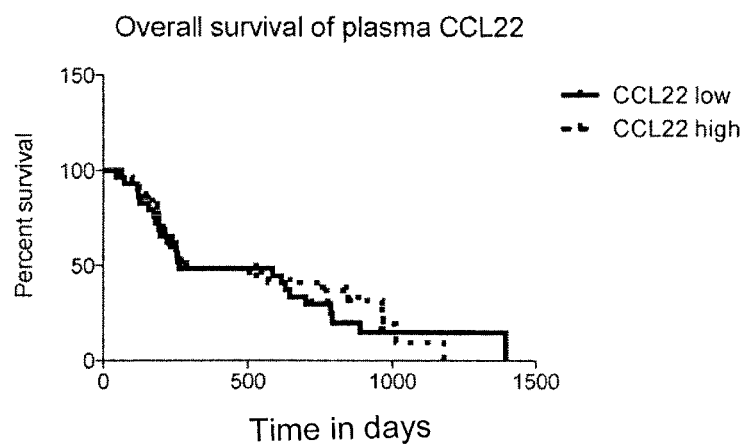

FIG. 7 Graph showing results of Example 2. Part A) shows progression-free survival and part B) shows overall survival plotted against time in days. The graph compares the outcome for patients with high CCL22 to the outcome for patients with low CCL22. The y-axis shows time in days.

Figure 8:
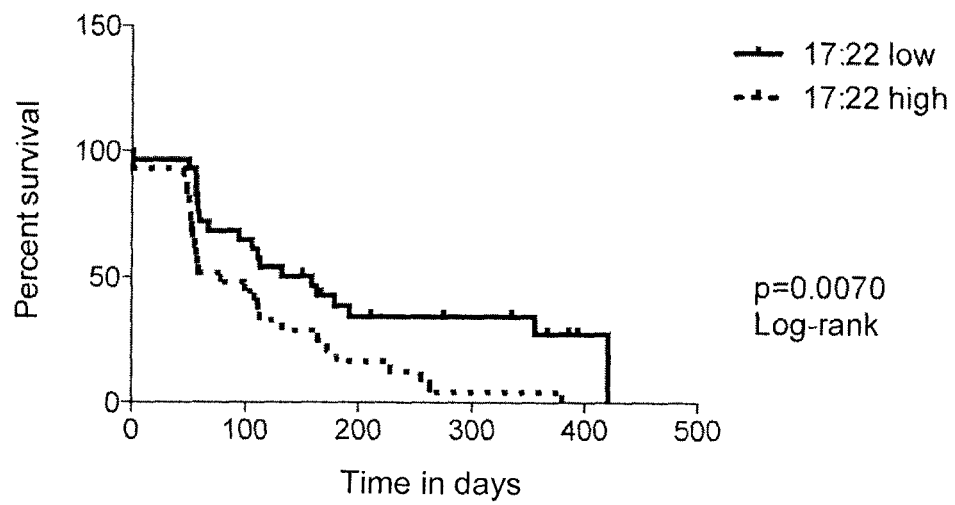
Figure 8:
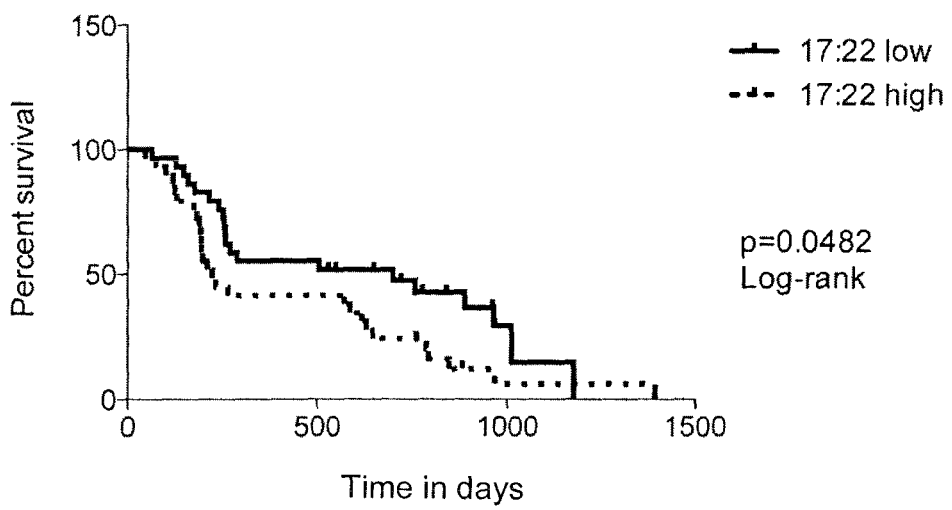

FIG. 8 Graph showing results of Example 2. Part A) shows progression-free survival and part B) shows overall survival plotted against time in days. The graph compares the outcome for patients with high CCL17:CCL22 ratio to the outcome for patients with low CCL17:CCL22 ratio. The y-axis shows time in days.

Figure 9:
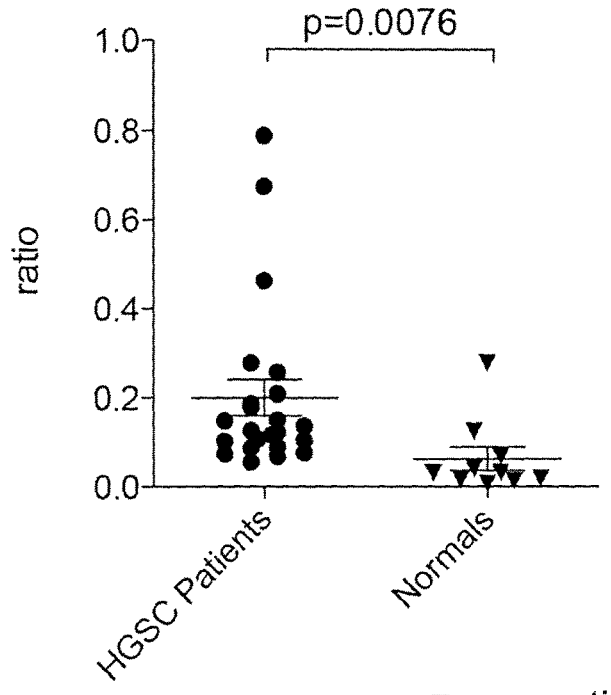

FIG. 9 Graph showing results of Example 3. The mean ratio of plasma CCL17:CCL22 in HGS ovarian cancer patients (all females) is significantly higher than the mean ratio of plasma CCL17:CCL22 in normal (healthy) female controls.

Figure 10:
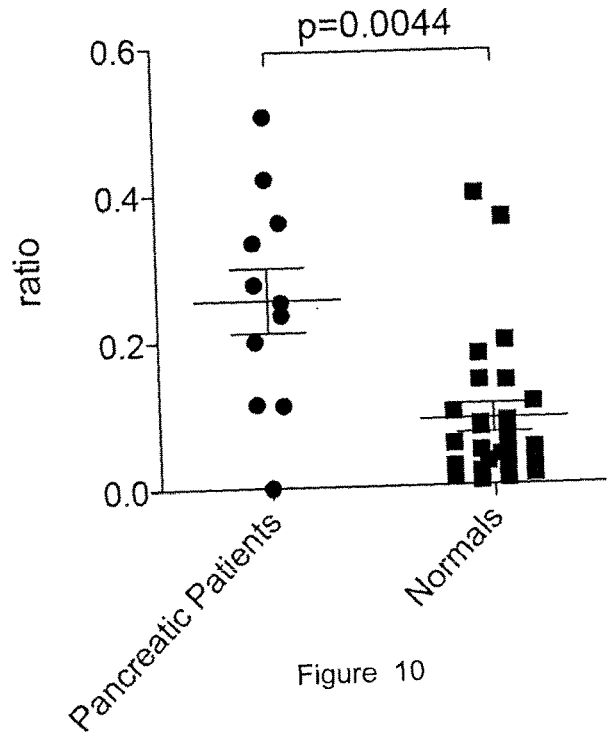

FIG. 10 Graph showing results of Example 3. The mean ratio of plasma CCL17:CCL22 in pancreatic cancer patients is significantly higher than the mean ratio of plasma CCL17:CCL22 in normal (healthy) controls.

Figure 11:
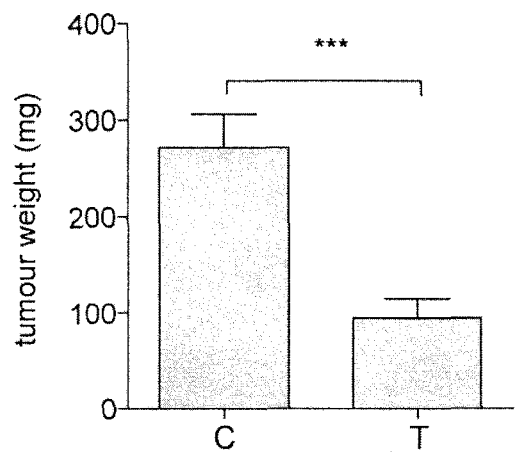

FIG. 11 Bar chart showing results of Example 4 (A). It shows the mean tumour weights at end point from three independent experiments with a total of twenty-three isotype control antibody-treated mice and twenty-one Affi-5-treated mice. Tumour weight of anti-CCR4 antibody (Affi-5)-treated animals (T) was significantly lower than tumour weight of control-treated animals (C). ***p<0.0001

Figure 12:
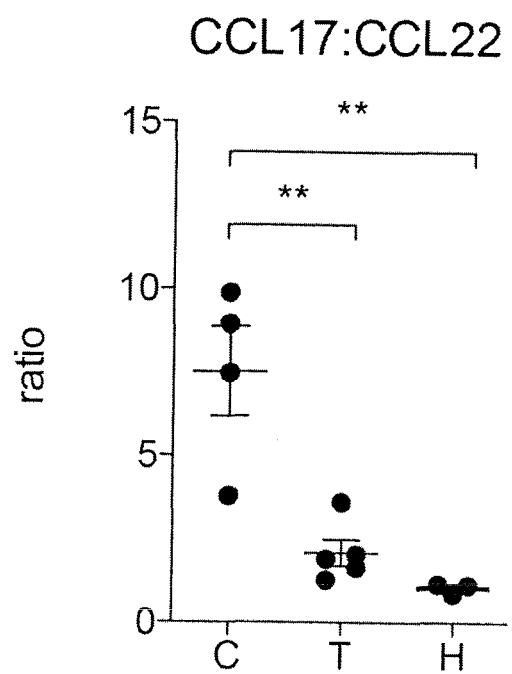

FIG. 12 Graph showing results of Example 4. The mean ratio of serum CCL17:CCL22 in anti-CCR4 antibody (Affi-5)-treated animals (T) was significantly lower than the mean ratio of serum CCL17:CCL22 in control-treated animals (C). Also shown in the mean ratio in serum of healthy animals (H), compared to which the control-treated mice have a significantly increased ratio, reflecting their tumour burden.

FIG. 13 Graph showing results of Example 4. The ratio of serum CCL17:CCL22 strongly correlates with tumour weight in mice.

Figure 14:
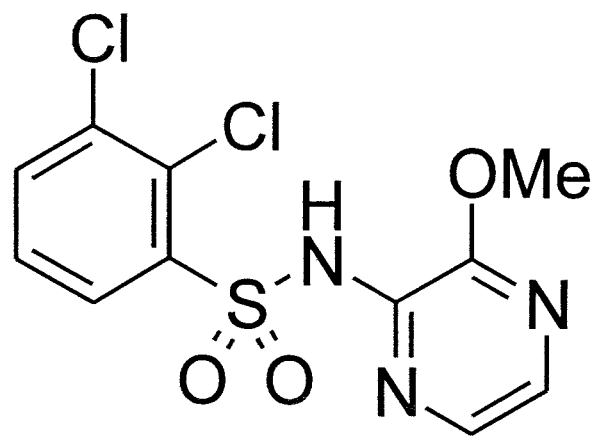

FIG. 14 Chemical formula of AZD2098, a chemical antagonist of CCR4.

Figure 15:
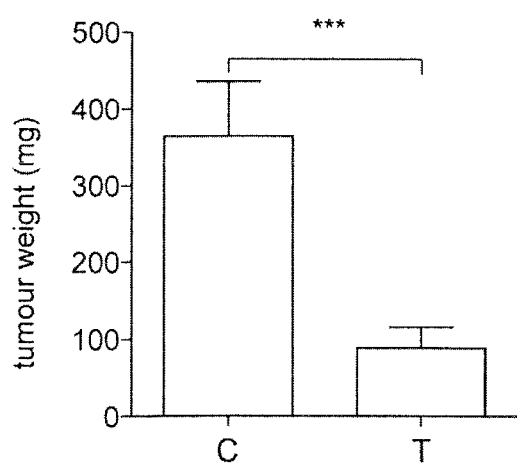

FIG. 15 Bar chart showing results of Example 5. It shows the mean tumour weights at end point from four independent experiments with a total of 27 control-vehicle treated mice and 28 AZD2098-treated mice. Tumour weight of AZD2098-treated animals (T) was significantly lower than tumour weight of control-treated animals (C). ***p=0.001.

Figure 16:
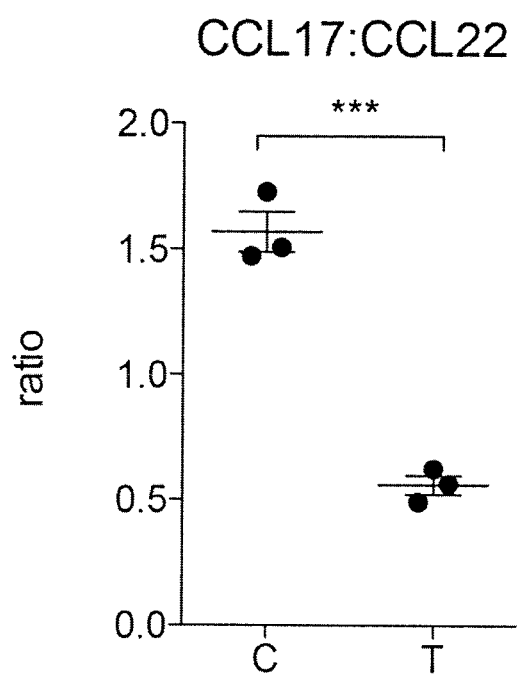

FIG. 16 Graph showing results of Example 5. The mean ratio of plasma CCL17:CCL22 in AZD2098-treated animals (T) was significantly lower than the mean ratio of plasma CCL17:CCL22 in control-treated animals (C).

EXAMPLES

Example 1

Biomarker Studies in Renal Cancer Biopsies and Cell Lines

CCR4 mRNA was measured by real-time RT-PCR in renal cancer biopsies and compared with normal kidney. This analysis of mRNA from normal and malignant human kidney biopsies revealed the expression of CCR4 mRNA in the malignant kidney, but not in the normal kidney samples (FIG. 1).
In order to further investigate CCR4 expression in human renal cancer, we stained a renal cancer tissue microarray, TMA, for CCR4 and its ligands using immunohistochemistry (IHC). The TMA was mainly comprised of clear cell renal carcinomas (75%), with some biopsies classified as papillary renal cancer.

CCR4 was detected on the malignant cells from 153 of 173 malignant tumour cores from 57 patients with advanced renal cell carcinoma (RCC), clear cell and non-clear cell, in our TMA (FIG. 2). Human spleen, which served as our positive control, also expressed CCR4 (not shown). The negative control tissue was placenta, and this did not express CCR4 (not shown). Infiltrating leukocytes also expressed CCR4 in the biopsies. The CCR4 ligands CCL17 and CCL22 were also found in the renal cancer biopsies (FIG. 2). In normal kidney tissue biopsies, we found very weak expression for CCR4 and CCL17 and weak expression of CCL22 (not shown). These studies confirm earlier reports that CCR4 and its ligands are abnormally expressed in malignant renal tissues.

Having detected CCR4 and its ligands in RCC biopsies, we then investigated whether these markers were present in cell lines established from renal cancer. Cell surface CCR4, as well as intracellular CCL17 and CCL22, were detected in human clear cell renal cell carcinoma cell lines 786-O and A498 and in the murine RCC cell line RENCA (data not shown).

We confirmed that CCR4 was functional on these RCC cell lines using CCL17 and CCL22 to stimulate migration in Transwell© migration assays. FIGS. 3 and 4 show bell-shaped dose response curves typical of chemokines to three concentrations of recombinant human or murine CCL17 and CCL22 in 786-O and RENCA cells respectively. This shows that cell surface CCR4 expressed on the surface of RCC cells is functional and, in spite of constitutive production of picogram quantities of ligand, the cell lines could still respond to external gradients.

Example 2

Plasma Analysis of Renal Cancer Patients

We measured levels of the CCR4 ligands CCL17 and CCL22 in plasma from 48 RCC patients and compared these to 26 normal plasma samples from age-matched individuals. CCL22 and CCL17 plasma levels were determined utilising the Meso Scale Discovery™ (MSD) System multiplex assay for human inflammatory chemokines K15001C-2 according to manufacturer's instructions.

The following is a brief overview of the assay system: MSD provides a plate that has been pre-coated with capture antibody on spatially distinct spots—antibodies for chemokines including CCL17 and CCL22. The user adds the sample and a solution containing the labeled detection antibodies—anti-CCL17 and anti-CCL22 labeled with an electrochemiluminescent compound, MSD SULFO-TAG label—over the course of one or more incubation periods. Analytes in the sample bind to capture antibodies immobilized on the working electrode surface; recruitment of the labeled detection antibodies by bound analytes completes the sandwich. The user adds an MSD read buffer that provides the appropriate chemical environment for electrochemiluminescence and loads the plate into an MSD SECTOR® instrument for analysis. Inside the SECTOR instrument, a voltage applied to the plate electrodes causes the labels bound to the electrode surface to emit light. The instrument measures intensity of emitted light to provide a quantitative measure of CCL17 or CCL22.

Circulating CCL17 and CCL22 levels were a mean of 756 and 1893 pg/ml respectively in the patients and 375 and 6805 pg/ml in the normal controls. Thus, CCL17 levels were higher in plasma of cancer patients than in healthy controls, but levels of CCL22 were lower in plasma of cancer patients than in healthy controls.

We surprisingly found that the ratio of CCL17 to CCL22 in plasma was a statistically significant indicator of cancer status, particularly tumour burden. As shown in FIG. 5, the majority of the normal, i.e. non-cancerous, control subjects assayed had a very low plasma CCL17:CCL22 ratio, whereas the majority of the renal cancer patients assayed had a high plasma CCL17:CCL22 ratio. In particular, the mean ratio was significantly higher in renal cancer patients versus healthy control (FIG. 5). An increased ratio (compared to healthy controls) is thus indicative of the presence of cancer.

We also investigated the relationship between these markers and survival. Plasma CCL17 and CCL22 levels were measured and patients were grouped into a group having a "high" level if their level was above the median and a group having a "low" level if their level was below the median. As shown in FIGS. 6 and 7, neither CCL17 nor CCL22 plasma levels alone were useful markers of progression-free survival or overall survival. However, the ratio of plasma CCL17:CCL22 was surprisingly a statistically significant marker of both overall survival and progression-free survival (FIG. 8). Patients were grouped into a group having a "high" ratio if their ratio was above the median and a group having a "low" ratio if their ratio was below the median. A high CCL17:CCL22 ratio was associated with lower progression-free and overall survival (p=0.007 and p=0.05 respectively).

Table 1 shows data generated as part of this work and an analysis thereof.

Example 3

Plasma Analysis of Further Cancer Patients

Having established that the ratio of plasma CCL17:CCL22 is a diagnostic and prognostic biomarker in renal cancer, we investigated whether this relationship also exists in other cancer types. We assayed pancreatic cancer and ovarian cancer (high grade serous ovarian cancer, HGS) and confirmed that in these cancers the ratio of plasma CCL17:CCL22 is also a statistically significant cancer marker (FIGS. 9 and 10).

Tables 1 and 2 show data generated as part of this work and an analysis thereof.

Example 4

Response to Treatment with Anti-CCR4 Antibody

We determined that a fully human IgG1 antibody antagonistic for CCR4 (denoted Affi-5, obtained from Affitech Research AS, Gaustadalléen 21, N-0349, Oslo, Norway) inhibits migration of 768-O and A498 cells to CCL17 in Transwell© migration assays. Briefly, 786-O or RENCA cells were harvested with EDTA-based buffer, resuspended in medium (serum-free for 786-O, containing 0.5% serum for RENCA), and pre-incubated with Affi-5 or control IgG for 45 minutes. $1-2\times10^5$ cells were seeded on top of Transwell© inserts (12-well format) and medium containing the indicated concentrations of human CCL17 (Peprotech) or mouse CCL17 (R&D, 1-001-A) was added in the bottom space. After an overnight incubation, Transwell© inserts were stained with a modified GIEMSA staining after removing cells remaining on top of the insert with a cotton bud. Membranes were excised from the insert and mounted on slides. Cell number in 10 fields per insert was counted at the microscope with a 40× magnification. Triplicates for each condition were analysed. Migration of RENCA cells to murine CCL17 was inhibited showing that the antibody was also antagonistic to murine CCR4.

The action of Affi-5 on RENCA cell migration led us to test this antibody in an in vivo RENCA model, RENCA cells were grown orthotopically in wild-type Balb/c mice by injection of luciferase-labelled RENCA cells under the renal capsule of the left kidney. Mice were given twice-weekly intraperitoneal injections of 10 mg/kg antibody or an isotype control.

Balb/c mice were orthotopically injected with $1\times104$ RENCA-luc cells and treatment with Affi5 (T) or IgG control (C), 10 mg/kg, was started 48 hours after surgery and continued twice weekly. Mice were sacrificed 17 days after surgery and tumour weight was determined by subtracting the weight of the right kidney (untreated) to the left kidney weight (tumour-bearing). Combined results from three experiments (n=28 control treated, n=27 treated) are shown. To determine luminescence, mice were injected i.p. with 150 μg/g body weight D-luciferin in PBS, and bioluminescence imaging with a charge-coupled device camera (IVIS, Xenogen, Alameda, Calif.) was initiated 10 min after injection. Imaging was performed at day 2, 7, 14, and 21.

FIG. 11 shows the mean tumour weights at end point from three independent experiments with a total of twenty-three isotype control antibody-treated mice and twenty-one Affi-5-treated mice. Antibody treatment caused a significant inhibition of tumour burden as measured by tumour weight or bioluminescence (p<0.0001).

As shown in FIG. 12, the serum CCL17:CCL22 ratio decreased with treatment response, i.e. the mean ratio of control-treated animals was significantly higher than the mean ratio of antibody-treated animals.

FIG. 13 shows that the ratio of serum CCL17:CCL22 strongly correlates with tumour weight in mice. This Figure shows the correlation of tumour weight with the ratio in mice treated with an anti-CCR4 agent and in untreated/control treated mice, illustrating that this correlation exists irrespective of treatment.

Example 5

Response to Treatment with Chemical Antagonist of CCR4

An study equivalent to the one described in Example 4 was carried out using a chemical antagonist of CCR4, a compound denoted AZD2098 having the chemical formula shown in FIG. 14.

A Transwell© migration assay, carried out essentially as described in Example 4 but with AZD2098 and instead of Affi-5, showed that AZD2098 inhibited migration of RENCA cells to murine CCL17, showing that the compound was antagonistic to murine CCR4.

An in vivo RENCA model assay was carried out essentially as described in Example 4 but with AZD2098 and instead of Affi-5. Four experiments (n=27 control treated, n=28 treated) were carried out and the results were combined. The results showed that AZD2098 treatment caused a significant inhibition of tumour burden as measured by of tumour weights (p=0.001) (FIG. 15) or bioluminescence (p=0.05).

The CCL17:CCL22 ratio was determined in plasma samples, rather than serum samples, of the animals. As shown in FIG. 16, the plasma CCL17:CCL22 ratio decreased with treatment response, i.e. the mean ratio of control-treated animals was significantly higher than the mean ratio of antagonist-treated animals.

The invention claimed is:

1. A method of diagnosing and treating cancer in a patient, said method comprising:
   a) measuring the level of CCL17 in a blood, plasma or serum sample from said patient;
   b) measuring the level of CCL22 in a blood, plasma or serum sample from said patient;
   c) determining the ratio of said CCL17 level to said CCL22 level;
   d) comparing said determined ratio to a control or reference ratio;
   e) diagnosing said patient with cancer if said ratio is increased; and
   f) administering an effective amount of an anti-CCR4 treatment to said diagnosed patient, wherein said anti-CCR4 treatment is selected from the group consisting of (i) an antibody which binds directly to CCR4, CCL17 or CCL22, and(ii) a chemical CCR4 antagonist.

2. A method according to claim 1, wherein said method involves determining the levels of CCL17 and CCL22 using antibodies.

3. A method according to claim 1, wherein said cancer is a carcinoma.

4. A method according to claim 1, wherein said cancer is selected from renal cancer, ovarian cancer and pancreatic cancer.

5. A method of monitoring the progression of cancer and treating said cancer in a patient, said method comprising:
   a) measuring the level of CCL17 in a blood, plasma or serum sample from said patient;
   b) measuring the level of CCL22 in a blood, plasma or serum sample from said patient;
   c) determining the ratio of said CCL17 level to said CCL22 level;
   d) comparing said determined ratio to a control or reference ratio;
   e) determining that said cancer has progressed if said ratio is increased; and
   f) administering an effective amount of an anti-CCR4 treatment to said patient whose cancer has progressed, wherein said anti-CCR4 treatment is selected from the group consisting of (i) an antibody which binds directly to CCR4, CCL17 or CCL22, and(ii) a chemical CCR4 antagonist.

6. A method according to claim 5, wherein said method involves determining the levels of CCL17 and CCL22 using antibodies.

7. A method according to claim 5, wherein said cancer is a carcinoma.

8. A method according to claim 5, wherein said cancer is selected from renal cancer, ovarian cancer and pancreatic cancer.

9. A method of making a prognosis of cancer and treating said cancer in a patient, said method comprising:
   a) measuring the level of CCL17 in a blood, plasma or serum sample from said patient;
   b) measuring the level of CCL22 in a blood, plasma or serum sample from said patient;
   c) determining the ratio of said CCL17 level to said CCL22 level;
   d) comparing said determined ratio to a control or reference ratio;
   e) determining that said patient has an adverse cancer prognosis if said ratio is increased; and
   f) administering an effective amount of an anti-CCR4 treatment to said patient with an adverse cancer prognosis, wherein said anti-CCR4 treatment is selected from the group consisting of (i) an antibody which binds directly to CCR4, CCL17 or CCL22, and (ii) a chemical CCR4 antagonist.

10. A method according to claim 9, wherein said method involves determining the levels of CCL17 and CCL22 using antibodies.

11. A method according to claim 9, wherein said cancer is a carcinoma.

12. A method according to claim 9, wherein said cancer is selected from renal cancer, ovarian cancer and pancreatic cancer.

13. A method of predicting the response of a cancer to an anti-CCR4 treatment and treating said cancer in a patient, said method comprising:
   a) measuring the level of CCL17 in a blood, plasma or serum sample from said patient;
   b) measuring the level of CCL22 in a blood, plasma or serum sample from said patient;
   c) determining the ratio of said CCL17 level to said CCL22 level;
   d) comparing said determined ratio to a control or reference ratio;
   e) determining that said cancer has an increased likelihood of responding to said treatment if said ratio is increased; and
   f) administering an effective amount of an anti-CCR4 treatment to said patient having a cancer with an increased likelihood of responding to said treatment, wherein said anti-CCR4 treatment is selected from the group consisting of (i) an antibody which binds directly to CCR4, CCL17 or CCL22, and(ii) a chemical CCR4 antagonist.

14. A method according to claim 13, wherein said method involves determining the levels of CCL17 and CCL22 using antibodies.

15. A method according to claim 13, wherein said cancer is a carcinoma.

16. A method according to claim 13, wherein said cancer is selected from renal cancer, ovarian cancer and pancreatic cancer.

17. A method of treating a cancer in a patient, said method comprising administering an effective amount of an anti-CCR4 treatment to said patient, wherein said patient was previously diagnosed with having cancer, having a poor cancer prognosis, or having a cancer that has progressed, based on a method comprising
   a) measuring the level of CCL17 in a blood, plasma or serum sample from said patient;
   b) measuring the level of CCL22 in a blood, plasma or serum sample from said patient;
   c) determining the ratio of said CCL17 level to said CCL22 level;
   d) comparing said determined ratio to a control or reference ratio; and
   e) diagnosing said patient with having cancer, having a poor cancer prognosis, or having a cancer that has progressed, if said ratio is increased, wherein said anti-CCR4 treatment is selected from the group consisting of (i) an antibody which binds directly to CCR4, CCL17 or CCL22, and(ii) a chemical CCR4 antagonist.

18. A method according to claim 17, wherein said cancer is a carcinoma.

19. A method according to claim 17, wherein said cancer is selected from renal cancer, ovarian cancer and pancreatic cancer.

20. A method of treating a cancer in a patient, said method comprising administering an effective amount of an anti- CCR4 treatment to said patient, wherein said cancer was previously predicted to have an increased likelihood of responding to an anti-cancer treatment based on a method comprising a) measuring the level of CCL17 in a blood, plasma or serum sample from said patient;

b) measuring the level of CCL22 in a blood, plasma or serum sample from said patient;

c) determining the ratio of said CCL17 level to said CCL22 level;

d) comparing said determined ratio to a control or reference ratio; and e) predicting that said cancer has an increased likelihood of responding to an anti-cancer treatment if said ratio is increased, wherein said anti-CCR4 treatment is selected from the group consisting of (i) an antibody which binds directly to CCR4, CCL17 or CCL22, and(ii) a chemical CCR4 antagonist.

21. A method according to claim 20, wherein said method involves measuring the levels of CCL17 and CCL22 using antibodies.

22. A method according to claim 20, wherein said cancer is a carcinoma.

23. A method according to claim 20, wherein said cancer is selected from renal cancer, ovarian cancer and pancreatic cancer.

\* \* \* \* \*